United States Patent
Schattner

(10) Patent No.: US 6,586,477 B1
(45) Date of Patent: Jul. 1, 2003

(54) TEAT DIP COMPOSITION CONTAINING PHENOL AND PHENATE

(75) Inventor: Robert I. Schattner, Bethesda, MD (US)

(73) Assignee: Sporicidin Company, Rockville, MD (US)

(*) Notice: Subject to any disclaimer, the term of this patent is extended or adjusted under 35 U.S.C. 154(b) by 0 days.

(21) Appl. No.: 10/284,824

(22) Filed: Oct. 31, 2002

(51) Int. Cl.[7] .............................................. A01N 31/08
(52) U.S. Cl. ...................................................... 514/731
(58) Field of Search .......................................... 514/731

(56) References Cited

U.S. PATENT DOCUMENTS

| | | | |
|---|---|---|---|
| 3,317,376 A | | 5/1967 | Schattner |
| 3,674,458 A | | 7/1972 | Schattner |
| 3,917,850 A | * | 11/1975 | Boucher ...................... 424/333 |
| 4,446,153 A | | 5/1984 | Yang |
| 4,642,267 A | | 2/1987 | Creasy et al. |
| 5,211,961 A | | 5/1993 | Adkinson |
| 5,503,838 A | * | 4/1996 | Schmidt et al. .............. 424/407 |
| 5,643,608 A | | 7/1997 | McKenzie et al. |
| 5,720,984 A | * | 2/1998 | Ricketts ...................... 424/672 |
| 5,840,765 A | | 11/1998 | Miller |
| 5,968,539 A | | 10/1999 | Beerse et al. |
| 5,980,925 A | | 11/1999 | Jampani et al. |
| 6,019,941 A | | 2/2000 | Porcello |
| 6,258,368 B1 | | 7/2001 | Beerse et al. |
| 6,379,685 B1 | * | 4/2002 | Richter et al. .............. 424/405 |
| 6,399,108 B1 | | 6/2002 | Girvan |
| 6,414,036 B1 | | 7/2002 | Ninkov |
| 2002/0072288 A1 | | 6/2002 | Hei et al. |
| 2002/0098160 A1 | | 7/2002 | Chowhan et al. |
| 2002/0103261 A1 | | 8/2002 | Ninkov |

* cited by examiner

*Primary Examiner*—Raymond Henley, III
(74) *Attorney, Agent, or Firm*—Hovey Williams LLP

(57) ABSTRACT

Aqueous germicidal compositions comprising a phenolic compound and a phenate and methods of treating animal skin with the compositions are provided. The compositions have a pH of from about 6–10 and comprise from about 1–2% by weight of a phenolic compound and a quantity of phenate to give a phenolic compound to phenate weight ratio of from about 0.81:1 to 10,000:1.

39 Claims, No Drawings

TEAT DIP COMPOSITION CONTAINING PHENOL AND PHENATE

BACKGROUND OF THE INVENTION

1. Field of the Invention

The present invention is broadly concerned with aqueous germicidal compositions comprising a phenolic compound and a phenate and methods of treating the skin of animals by applying the compositions thereto.

2. Description of the Prior Art

A number of antibacterial agents are used as topical antiseptics designed to reduce intramammary infections in dairy cows and other milk producing) animals such as goats and sheep. These products, typically referred to as teat dips, generally serve to disinfect the teat skin surface and teat orifice and maintain overall skin health. In practical use, teat dips are applied by dipping or spraying the composition onto the teats of the animals following removal of the mechanical milking devices used to extract milk from the udder. The use of teat dips has proven effective in reducing the incidence rate of new intramammary infections by decreasing the exposure of the udder to mastitis causing pathogens that may be present in the residual milk film remaining on the surface of the teat skin. In some instances, teat dips are applied prior to the milking process in order to reduce exposure to pathogens which are present in the animal's environment and which reside on the teat skin surface through incidental contact.

Teat dips are commonly provided in the form of aqueous solutions which include germicidal agents such as iodine, chlorhexidene salts, sodium hypochlorite, chlorine dioxide, hydrogen peroxide, or antibacterial anionic surfactants. Because teat dips are used on food producing animals, care must be taken in the selection and use of germicidal agents so that residues which inadvertently find their way into the food product do not pose a health risk to the consumer. Phenol and various halogenated and alkylated derivatives have been used as germicides for over a century. Phenol is considered non-toxic and safe at relatively low concentrations as demonstrated by its use in FDA approved over-the-counter drug applications such as throat sprays.

U.S. Pat. No. 3,317,376 describes the use of phenol/sodium phenolate (phenate) solutions for rendering fabrics germicidal and bactericidal. Concentrations of phenol range from 2–16.5% by weight, and the ratios of phenol to sodium phenate range from 0.37 to 20.

U.S. Pat. No. 3,917,850 describes a biocide composition for surface and space disinfection comprising an aldehyde and/or dialdehyde and a phenol derivative in a solvent. Concentrations of phenol derivatives range from about 15–45% by weight.

However, phenolic compositions have not been employed in topical germicidal compositions for use in treating mammalian skin. Therefore, there is a real and unfulfilled need in the art for a composition including an effective germicidal agent that is non-toxic and safe for use on food producing animals in addition to promoting the overall health of animal skin.

SUMMARY OF THE INVENTION

The present invention overcomes the problems outlined above and provides an aqueous germicidal composition comprising from about 1–2% by weight of a phenolic compound and a quantity of a phenate. Preferably the composition has a pH of from about 6–10, more preferably from about 6.5–8.5, and most preferably from about 7–8 and a phenolic compound to phenate weight ratio of from about 0.81:1 to 10,000:1, more preferably from about 25:1 to 2,600:1, and most preferably from about 80:1 to 800:1. All weight percentages expressed herein are based on the weight of the entire composition being 100%.

Compositions according to the present invention further comprise a buffering agent for pH control. Preferred buffering agents include those selected from the group consisting of salts of boric acid, phosphoric acid, citric acid, carbonic acid, and mixtures thereof. Sodium tetraborate decahydrate is an exemplary preferred buffering agent for use with the present invention. Other buffering agents may be chosen depending on the exact pH desired for a given application of the composition. Preferably the compositions will comprise from about 0.02–2.0% by weight and most preferably from about 0.25–0.75% by weight of buffering agent.

Preferred embodiments of the present invention comprise from about 1–2% by weight, more preferably from about 1.2–1.8% by weight, and most preferably 1.4–1.7% by weight of a phenolic compound. As used herein, the term "phenolic compound" refers to any aromatic hydroxylated compound or derivative thereof, or any compound derived from or containing phenol. Preferred phenolic compounds for use with the present invention are selected from the group consisting of phenol, halogen substituted, alkyl substituted, halogen and alkyl substituted phenol derivatives, bisphenol, halogen substituted, alkyl substituted, halogen and alkyl substituted bisphenol derivatives, and mixtures thereof.

As used herein, the term "phenate" includes derivatives of phenolic compounds wherein the hydrogen from the hydroxyl group has dissociated therefrom or has been replaced with a monovalent metal. Preferably the phenate is derived from the phenolic compound, that is, the phenate is formed by the removal of hydrogen from the hydroxyl group of the phenol.

It is preferable that compositions according to the present invention include at least one component selected from the group consisting of a wetting agent, an emollient, and a thickener. It is most preferable that such compositions include all three components.

Preferred compositions of the present invention comprise from about 0.01–2% by weight, and more preferably from about 0.05–1.5% by weight of a wetting agent, from about 0.5–15% by weight, more preferably from about 2–10% by weight, and most preferably from about 5–10% by weight of an emollient, and from about 0.02–1.0% by weight, more preferably from about 0.05–0.6% by weight, and most preferably from about 0.06–0.3% by weight of a thickener.

Preferred wetting agents for use with the present invention include anionic surfactants, cationic surfactants, non-ionic surfactants, amphoteric surfactants, and mixtures thereof. Preferred emollients for use with the present invention include glycerin, propylene glycol, sorbitol, allantoin, ethoxylated lanolin, aloe vera extracts and mixtures thereof. Preferred thickeners for use with the present invention include alginates, natural gums, cellulosic polymers and mixtures thereof.

Coloring agents, such as pigments or dyes, may be added to compositions prepared in accordance with the present invention. Preferred coloring agents for use with the present invention comprise any organic or inorganic dye which is a chemically acceptable trace constituent on the animal skin to which it is to be applied and the resulting food product derived from the animal. Such dyes are generally those approved for use in drug products by various regulatory bodies. Preferred coloring agents include FD&C Yellow No. 5, FD&C Blue No. 1, and FD&C Yellow No. 6. Generally, the coloring agent will be present in a concentration of from about 0.001–0.5% by weight and preferably from about 0.01–0.3% by weight.

Methods of treating animal skin according to the present invention comprise the steps of providing an aqueous germicidal composition comprising a quantity of a phenolic compound, adjusting the pH of the composition to between about 6–10, more preferably to between about 6.5–8.5, and most preferably to between about 7–8 thereby converting a portion of the phenolic compound to a phenate, and applying the compound to the skin of an animal. The composition may be applied to the animal skin by dipping, spraying, or foaming the composition onto the animal skin, or by any other means known to those skilled in the art. Preferably, the animal skin to be treated according to the invention is the skin of a bovine teat. The weight ratio of the phenolic compound to phenate is preferably from about 0.81:1 to 10,000:1, and more preferably from about 25:1 to 2,600:1, and most preferably from about 80:1 to 800:1. Preferred germicidal compositions for use with methods of the present invention include any composition produced in accordance with the invention as described above.

DETAILED DESCRIPTION OF THE PREFERRED EMBODIMENT

Compositions of the present invention comprise aqueous solutions of phenol and/or one or more of its many substituted derivatives. Such derivatives include those known in the art and include, but are not limited to, halogenated phenols, ortho-, meta-, and para-substituted chlorophenols and bromophenols, di-halogenated phenols, various alkylated phenols such as ortho-, meta-, and para-substituted methyl, ethyl, n-propyl, n-butyl, n-amyl, n-hexyl, tertiary amyl, tertiary butyl, and cyclohexyl phenols, and alkyl and halogen substituted phenols. Bisphenols, compounds comprising two phenolic groups connected by various linkages, are also suitable for use with the present invention. Such compounds include, but are not limited to 2,2-methylene-bis(4,6-dichlorophenol) and 2,2-methylene-bis(3,4,6-trichlorophenol). The following is a non-exclusive list of preferred phenolic compounds for use in compositions according to the present invention and should not be considered as a limitation on the overall scope of phenolic compounds which may be used in the present invention.

Phenol
2-Methyl Phenol
3-Methyl Phenol
4-Methyl Phenol
4-Ethyl Phenol
2,4-Dimethyl Phenol
2,5-Dimethyl Phenol
3,4-Dimethyl Phenol
2,6-Dimethyl Phenol
4-n-Propyl Phenol
4-n-Butyl Phenol
4-n-Amyl Phenol
4-tert-Amyl Phenol
4-n-Hexyl Phenol
4-n-Heptyl Phenol
Mono- and Poly-Alkyl and Aromatic Halophenols
p-Chlorophenol
Methyl p-Chlorophenol
Ethyl p-Chlorophenol
n-Propyl p-Chlorophenol
n-Butyl p-Chlorophenol
n-Amyl p-Chlorophenol
sec-Amyl p-Chlorophenol
n-Hexyl p-Chlorophenol
Cyclohexyl p-Chlorophenol
n-Heptyl p-Chlorophenol
n-Octyl p-Chlorophenol
o-Chlorophenol
Methyl o-Chlorophenol
Ethyl o-Chlorophenol
n-Propyl o-Chlorophenol
n-Butyl o-Chlorophenol
n-Amyl o-Chlorophenol
tert-Amyl o-Chlorophenol
n-Hexyl o-Chlorophenol
n-Heptyl o-Chlorophenol
o-Benzyl p-Chlorophenol
o-Benzyl-m-methyl p-Chlorophenol
o-Benzyl-m, m-dimethyl p-Chlorophenol
o-Phenylethyl p-Chlorophenol
o-Phenylethyl-n-methyl p-Chlorophenol
3-Methyl p-Chlorophenol
3,5-Dimethyl p-Chlorophenol
6-Ethyl-3-methyl p-Chlorophenol
6-n-Propyl-3-methyl p-Chlorophenol
6-iso-Propyl-3-methyl p-Chlorophenol
2-Ethyl-3,5-dimethyl p-Chlorophenol
6-sec-Butyl-3-methyl p-Chlorophenol
2-iso-Propyl-3,5-dimethyl p-Chlorophenol
6-Diethylmethyl-3-methyl p-Chlorophenol
6-iso-Propyl-2-ethyl-3-methyl p-Chlorophenol
2-sec-Amyl-3,5-dimethyl p-Chlorophenol
2-Diethylmethyl-3,5-dimethyl p-Chlorophenol
6-sec-Octyl-3-methyl p-Chlorophenol
p-Chloro-m-cresol
p-Bromophenol
Methyl p-Bromophenol
Ethyl p-Bromophenol
n-Propyl p-Bromophenol
n-Butyl p-Bromophenol
n-Amyl p-Bromophenol
sec-Amyl p-Bromophenol
n-Hexyl p-Bromophenol
Cyclohexyl p-Bromophenol
o-Bromophenol
tert-Amyl o-Bromophenol
n-Hexyl o-Bromophenol
n-Propyl-m,m-Dimethyl o-Bromophenol
2-Phenyl Phenol
4-Chloro-2-methyl phenol
4-Chloro-3-methyl phenol
4-Chloro-3,5-dimethyl phenol
2,4-Dichloro-3,5-dimethylphenol
3,4,5,6-Tetrabromo-2-methylphenol
5-Methyl-2-pentylphenol
4-Isopropyl-3-methylphenol
Para-chloro-meta-xylenol (PCMX)
Chlorothymol
Phenoxyethanol
Phenoxyisopropanol
5-Chloro-2-hydroxydiphenylmethane
Resorcinol
Methyl Resorcinol
Ethyl Resorcinol
n-Propyl Resorcinol n-Butyl Resorcinol
n-Amyl Resorcinol
n-Hexyl Resorcinol
n-Heptyl Resorcinol
n-Octyl Resorcinol
n-Nonyl Resorcinol
Phenyl Resorcinol
Benzyl Resorcinol
Phenylethyl Resorcinol
Phenylpropyl Resorcinol
p-Chlorobenzyl Resorcinol
5-Chloro 2,4-Dihydroxydiphenyl Methane
4'-Chloro 2,4-Dihydroxydiphenyl Methane
5-Bromo 2,4-Dihydroxydiphenyl Methane
4'-Bromo 2,4-Dihydroxydiphenyl Methane
2,2'-Methylene bis (4-chlorophenol)
2,2'-Methylene bis (3,4,6-trichlorophenol)
2,2'-Methylene bis (4-chloro-6-bromophenol)

Compounds according to the present invention preferably comprise a quantity of a phenate, and preferably the phenate is derived from the phenolic compound. The present invention has the advantage that the phenate does not need to be added to the composition as a separate component in the form of a phenate salt. Phenolic compounds are generally weak acids and will dissociate in aqueous solutions to varying degrees depending upon the pH of the final solution. The relative concentrations of the undissociated phenolic compound and the phenate can be calculated using the Henderson-Hasselbalch equation:

$$pH = pK_a - \log([acid]/[base])$$

where: pH=final pH of the solution $pK_a$=the negative log of the dissociation constant for the phenolic compound

[acid]=the molar concentration of the phenolic compound in the final solution

[base]=the molar concentration of the phenate in the final solution

Using phenol as an example, the following table illustrates the calculated concentrations of phenol and phenate generated for a given phenol solution at various pH values.

TABLE 1

| pH | Added Phenol Concentration (wt. % of 90%) | Phenol Concentration (wt. %) | Phenate Concentration (wt. %) | Ratio of Phenol to Phenate (weight basis) |
|---|---|---|---|---|
| 6.000 | 1.78 | 1.600 | 0.00020 | 8106 |
| 6.500 | 1.78 | 1.599 | 0.0006 | 2563 |
| 7.000 | 1.78 | 1.598 | 0.002 | 810 |
| 7.400 | 1.78 | 1.596 | 0.005 | 322 |
| 8.000 | 1.78 | 1.584 | 0.020 | 81.1 |
| 8.500 | 1.78 | 1.551 | 0.061 | 25.6 |
| 9.000 | 1.78 | 1.455 | 0.179 | 8.10 |
| 10.000 | 1.78 | 0.800 | 0.987 | 0.81 |

Wetting agents serve to enhance the contact of the germicidal composition with the skin surface. The wetting agent aids in providing for complete coverage of the contacted skin and increases penetration into fissures and cracks on the skin surface. Preferably, the wetting agent comprises a surfactant, and most preferably a surfactant selected from the group consisting of anionic, cationic, nonionic, and amphoteric surfactants.

Preferred anionic surfactants include but are not limited to: alkali metal salts, ammonium salts, amine salts, or amino alcohol salts of one or more of the following compounds: alkyl sulfates, alkylaryl sulfonates, alkyl sulfosuccinates, alkyl ether sulfosuccinates, alkyl phosphates, alkylamide sulfonates and alkyl ether phosphates. Generally, the alkyl or alkylaryl radical will comprise from about 8–22 carbon atoms. Particularly preferred anionic surfactants include sodium dodecyl benzene sulfonate and disodium dioctyl sulfosuccinate. Additional anionic surfactants which may be used with the present invention include salts of various fatty acids having carbon chain lengths of from about 8–22 carbon atoms. Exemplary fatty acid salts are salts of oleic, palmitic, stearic, and ricinoleic acids.

Preferred cationic surfactants include quaternary ammonium compounds and salts thereof. Particularly preferred quaternary ammonium compounds may be characterized by the general structural formula:

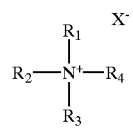

At least one of $R_1$, $R_2$, $R_3$, and $R_4$ is a hydrophobic, aliphatic, aryl aliphatic or aliphatic aryl radical of from about 6–26 carbon atoms, and the entire cation portion of the molecule has a molecular weight of at least 165. The hydrophobic radicals may be long-chain alkyl, long-chain alkoxy aryl, long-chain alkyl aryl, halogen-substituted long-chain alkyl aryl, long-chain alkyl phenoxy alkyl, and aryl alkyl. The remaining radicals on the nitrogen atom, other than the hydrophobic radicals, are substituents of a hydrocarbon structure usually containing a total of no more than 12 carbon atoms. The radical $X^-$ may be any salt-forming anionic radical.

Preferred amphoteric surfactants for use with the present invention include one or more of a variety of surfactants known in the art including betaines and ethylene oxide condensates of fatty acid amides. Further useful amphoteric surfactants include the salts of higher alkyl beta-amino propionic acids such as sodium N-lauryl beta-alanine, higher alkyl substituted betaines such as lauryl dimethylammonium acetic acid, and amphoteric surfactants of the imidazoline type exemplified by the disodium salt of 1-(2-hydroxyethyl)-1-1(carboxymethyl)-2-(hexadecyl)-4,5-dihydroimidazolinium hydroxide.

Preferred nonionic surfactants for use with the present invention include any nonionic surfactant compound known in the art. Practically any hydrophobic compound having a carboxy, hydroxy, amido, or amino group with a free hydrogen attached to the nitrogen can be condensed with ethylene oxide or with the polyhydration product thereof, such as polyethylene glycol, to form a water soluble nonionic surfactant compound. The length of the polyethylenoxy hydrophobic and hydrophilic elements may vary. Exemplary nonionic surfactant compounds include the polyoxyethylene ethers of alkyl aromatic hydroxy compounds such as alkylated polyoxyethylene phenols, polyoxyethylene ethers of long-chain aliphatic alcohols, the polyoxyethylene ethers of hydrophobic propylene oxide polymers, and the higher alkyl amine oxides.

The following example sets forth preferred compositions according to the present invention. It is to be understood, however, that these examples are provided by way of illustration and nothing therein should be taken as a limitation upon the overall scope of the invention.

EXAMPLE

A number of compositions were prepared in accordance with the invention, each containing 1.6% by weight active ingredient (phenol/phenate) and amounts of buffer, dye, thickener, and emollient. The pH of the compositions was varied by incorporation of either phosphoric acid or sodium hydroxide. These samples were subsequently tested for germicidal efficacy, using a 15 second exposure, against *Staphylococcus aureus* using the AOAC Germicidal and Detergent Sanitizers Test with a 10% whole milk challenge. The results are shown in Table 2.

TABLE 2

|  | pH 6 | pH 7 | pH 7.4 | pH 8 | pH 9 | pH 10 |
| --- | --- | --- | --- | --- | --- | --- |
| Phenol (90%) USP | 1.78% | 1.78% | 1.78% | 1.78% | 1.78% | 1.78% |
| Borax 10 Mol NF | 0.47% | 0.47% | 0.47% | 0.47% | 0.47% | 0.47% |
| Glycerin USP (99.5%) | 6.03% | 6.03% | 6.03% | 6.03% | 6.03% | 6.03% |
| FD&C Blue #1 | 0.015% | 0.015% | 0.015% | 0.015% | 0.015% | 0.015% |
| FD&C Yellow #5 | 0.01% | 0.01% | 0.01% | 0.01% | 0.01% | 0.01% |
| Keltrol RD (Xanthan gum) | 0.06% | 0.06% | 0.06% | 0.06% | 0.06% | 0.06% |
| Witconate 90F (sodium dodecyl benzene sulfonate) | 1.33% | 1.33% | 1.33% | 1.33% | 1.33% | 1.33% |
| Sodium hydroxide (50%) | 0 | 0 | 0 | qs to pH 8 | qs to pH 9 | qs to pH 10 |
| Phosphoric acid (85%) | qs to pH 6 | qs to pH 7 | 0 | 0 | 0 | 0 |
| Water | 90.305% | 90.305% | 90.305% | 90.305% | 90.305% | 90.305% |
| Phenol to Phenate Weight Ratio | 8106 | 810 | 322 | 81.1 | 8.1 | 0.811 |
| Log Reduction vs. S. aureus | 5.28 | 7.69 | 7.69 | 7.69 | 6.21 | 6.38 |

The compositions having pHs of 7, 7.4, and 8 were found to be the most effective in killing *S. aureus* compared to the other compositions. This result was surprising because, intuitively, it was expected that germicidal activity would be correlated with the amount of phenol in the solution, and that conversion to phenate may reduce the antibacterial properties of the composition. The observed maximum in activity vs. pH value runs counter to conventional thinking. As demonstrated above, the phenol to phenate ratio of the most effective compositions ranged from about 80:1 to 800:1.

I claim:

1. An aqueous germicidal composition comprising from about 1–2% by weight of a phenolic compound and a quantity of a phenate, said composition having a pH of from about 6–10 and a weight ratio of said phenolic compound to said phenate of from about 25:1 to 2,600:1.

2. The composition of claim 1, said composition having a pH of from about 6.5–8.5.

3. The composition of claim 1, said composition having a pH of from about 7–8.

4. The composition of claim 1, said weight ratio being from about 80:1 to 800:1.

5. The composition of claim 1, said phenate being derived from said phenolic compound.

6. The composition of claim 1, said phenolic compound selected from the group consisting of phenol, halogen substituted, alkyl substituted, and halogen and alkyl substituted phenol derivatives, bisphenol, halogen substituted, alkyl substituted, and halogen and alkyl substituted bisphenol derivatives, and mixtures thereof.

7. The composition of claim 6, said phenolic compound comprising phenol.

8. The composition of claim 1, said composition comprising at least one additional component selected from the group consisting of a wetting agent, an emollient, and a thickener.

9. The composition of claim 8, said wetting agent selected from the group consisting of anionic surfactants, cationic surfactants, nonionic surfactants, amphoteric surfactants, and mixtures thereof.

10. The composition of claim 8, said emollient selected from the group consisting of glycerin, propylene glycol, sorbitol, allantoin, ethoxylated lanolin, aloe vera extracts, and mixtures thereof.

11. The composition of claim 8, said thickener selected from the group consisting of alginates, natural gums, cellulosic polymers, and mixtures thereof.

12. An aqueous germicidal composition comprising:
from about 1–2% by weight of a phenolic compound;
from about 0.01–2% by weight of a wetting agent;
from about 0.5–15% by weight of an emollient; and
from about 0.02–1% by weight of a thickener,
said composition having a pH of from about 6–10.

13. The composition of claim 12, said composition having a pH of from about 6.5–8.5.

14. The composition of claim 12, said composition having a pH of from about 7–8.

15. The composition of claim 12, said phenolic compound selected from the group consisting of phenol, halogen substituted, alkyl substituted, and halogen and alkyl substituted phenol derivatives, bisphenol, halogen substituted, alkyl substituted, and halogen and alkyl substituted bisphenol derivatives, and mixtures thereof.

16. The composition of claim 15, said phenolic compound comprising phenol.

17. The composition of claim 12, said wetting agent selected from the group consisting of anionic surfactants, cationic surfactants, nonionic surfactants, amphoteric surfactants, and mixtures thereof.

18. The composition of claim 12, said emollient selected from the group consisting of glycerin, propylene glycol, sorbitol, allantoin, ethoxylated lanolin, aloe vera extracts, and mixtures thereof.

19. The composition of claim 12, said thickener selected from the group consisting of alginates, natural gums, cellulosic polymers, and mixtures thereof.

20. The composition of claim 12, said composition further comprising a phenate.

21. The composition of claim 20, said phenate being derived from said phenolic compound.

22. The composition of claim 20, the weight ratio of said phenolic compound to said phenate being from about 0.81:1 to 10,000:1.

23. The composition of claim 20, the weight ratio of said phenolic compound to said phenate being from about 25:1 to 2.600:1.

24. The composition of claim 20, the ratio of said phenolic compound to said phenate being from about 80:1 to 800:1.

25. A method of treating animal skin comprising the steps of:

providing an aqueous germicidal composition comprising a quantity of a phenolic compound;

adjusting the pH of the composition to between about 6–10 thereby converting a portion of said phenolic compound to a phenate, the weight ratio of said phenolic compound to said phenate being from about 0.81:1 to 10,000:1; and applying said composition to the skin of an animal.

26. The method of claim 25, said pH adjustment step comprising adjusting the pH of the composition to between about 6.5–8.5.

27. The method of claim 25, said pH adjustment step comprising adjusting the pH of the composition to between about 7–8.

28. The method of claim 25, said composition comprising from about 1–2% by weight of said phenolic compound.

29. The method of claim 25, said phenolic compound selected from the group consisting of phenol, halogen substituted, alkyl substituted, and halogen and alkyl substituted phenol derivatives, bisphenol, halogen substituted, alkyl substituted, and halogen and alkyl substituted bisphenol derivatives, and mixtures thereof.

30. The method of claim 29, said phenolic compound comprising phenol.

31. The method of claim 25, said composition comprising at least one additional component selected from the group consisting of a wetting agent, an emollient, and a thickener.

32. The method of claim 31, said wetting agent selected from the group consisting of anionic surfactants, cationic surfactants, nonionic surfactants, amphoteric surfactants, and mixtures thereof.

33. The method of claim 31, said emollient selected from the group consisting of glycerin, propylene glycol, sorbitol, allantoin, ethoxylated lanolin, aloe vera extracts, and mixtures thereof.

34. The method of claim 31, said thickener selected from the group consisting of alginates, natural gums, cellulosic polymers, and mixtures thereof.

35. The method of claim 25, the weight ratio of said phenolic compound to said phenate being from about 25:1 to 2,600:1.

36. The method of claim 25, the weight ratio of said phenolic compound to said phenate being from about 80:1 to 800:1.

37. The method of claim 25, said composition being applied to the skin of a bovine teat.

38. An aqueous germicidal composition comprising from about 1–2% by weight of a phenolic compound, a quantity of a phenate, and at least one additional component selected from the group consisting of a wetting agent, an emollient, and a thickener, said composition having a pH of from about 6–10 and a weight ratio of said phenolic compound to said phenate.of from about 0.81:1 to 10,000:1, said wetting agent selected from the group consisting of anionic surfactants, cationic surfactants, nonionic surfactants, amphoteric surfactants, and mixtures thereof.

39. An aqueous germicidal composition comprising from about 1–2% by weight of a phenolic compound, a quantity of a phenate, and at least one additional component selected from the group consisting of a wetting agent, an emollient, and a thickener, said composition having a pH of from about 6–10 and a weight ratio of said phenolic compound to said phenate of from about 0.81:1 to 10,000:1, said thickener selected from the group consisting of alginates, natural gums, cellulosic polymers, and mixtures thereof.

* * * * *